US012629392B2

(12) United States Patent
Jermy et al.

(10) Patent No.: US 12,629,392 B2
(45) Date of Patent: May 19, 2026

(54) METHOD OF TREATING COVID-19 INFECTION USING SUPERPARAMAGNETIC IRON OXIDE NANOPARTICLE

(71) Applicant: Imam Abdulrahman Bin Faisal University, Dammam (SA)

(72) Inventors: B. Rabindran Jermy, Dammam (SA); Vijaya Ravinayagam, Dammam (SA); Dana Almohazey, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 533 days.

(21) Appl. No.: 18/303,256

(22) Filed: Apr. 19, 2023

(65) Prior Publication Data

US 2024/0350537 A1     Oct. 24, 2024

(51) Int. Cl.

| | |
|---|---|
| *A61K 33/26* | (2006.01) |
| *A61K 31/4196* | (2006.01) |
| *A61K 31/722* | (2006.01) |
| *A61K 33/243* | (2019.01) |
| *A61K 47/69* | (2017.01) |
| *A61N 2/00* | (2006.01) |
| *A61P 31/14* | (2006.01) |
| *B82Y 5/00* | (2011.01) |
| *C12N 9/48* | (2006.01) |

(52) U.S. Cl.
CPC .......... *A61K 33/26* (2013.01); *A61K 31/4196* (2013.01); *A61K 31/722* (2013.01); *A61K 33/243* (2019.01); *A61K 47/6923* (2017.08); *A61N 2/002* (2013.01); *A61P 31/14* (2018.01); *B82Y 5/00* (2013.01); *C12N 9/485* (2013.01); *C12Y 304/17023* (2013.01)

(58) Field of Classification Search
None
See application file for complete search history.

(56) References Cited

U.S. PATENT DOCUMENTS

| | | | |
|---|---|---|---|
| 8,512,697 | B2 | 8/2013 | Fischer et al. |
| 9,849,194 | B2 | 12/2017 | Trabolsi et al. |
| 11,160,763 | B2 | 11/2021 | Jermy et al. |
| 2019/0091150 | A1 | 3/2019 | Brinker et al. |
| 2020/0338122 | A1* | 10/2020 | Jermy .................. A61K 33/243 |

FOREIGN PATENT DOCUMENTS

CN          113599536 A      11/2021

OTHER PUBLICATIONS

Ravinayagam, V; et al. "Nanodrug Delivery Systems for Infectious Diseases: From Challenges to Solutions", Chapter 13 in Nanotechnology for Infectious Diseases, (2022), 281-302, published Apr. 14, 2022. (Year: 2022).*

Mahdieh Darroudi, et al., "Fabrication and application of cisplatin-loaded mesoporous magnetic nanobiocomposite: a novel approach to smart cervical cancer chemotherapy", Cancer Nanotechnology, vol. 13, Article No. 36, Nov. 2, 2022, pp. 1-15.

Daniela J Hernández-Castillo, et al., "Selective etching of $SiO_2$-nanospheres as reservoirs for pH-sensitive release of cis-diamminedichloroplatinum(II)", Journal of Chemical Technology and Biotechnology, vol. 94, Issue 11, Jan. 13, 2019, pp. 3505-3511.

* cited by examiner

*Primary Examiner* — David J Blanchard
*Assistant Examiner* — Kaeleigh E Olsen
(74) *Attorney, Agent, or Firm* — Oblon, McClelland, Maier & Neustadt, L.L.P.

(57)          ABSTRACT
A method of treating a COVID-19 infection includes administering to a subject in need thereof an effective amount of a composition, where the composition includes silica nanoparticles, superparamagnetic iron oxide nanoparticles (SPIONs), chitosan, cisplatin, ribavirin, and an angiotensin-converting enzyme 2 (ACE-2). The SPIONs and ACE-2 are dispersed on an outer surface of the silica nanoparticles. The chitosan at least partially wraps around the outer surface of the silica nanoparticles. The cisplatin and ribavirin are in pores of the silica nanoparticles. The composition is in the form of particles that are monodisperse, are spherical, and have an average diameter of 70-100 nanometers (nm).

20 Claims, 10 Drawing Sheets

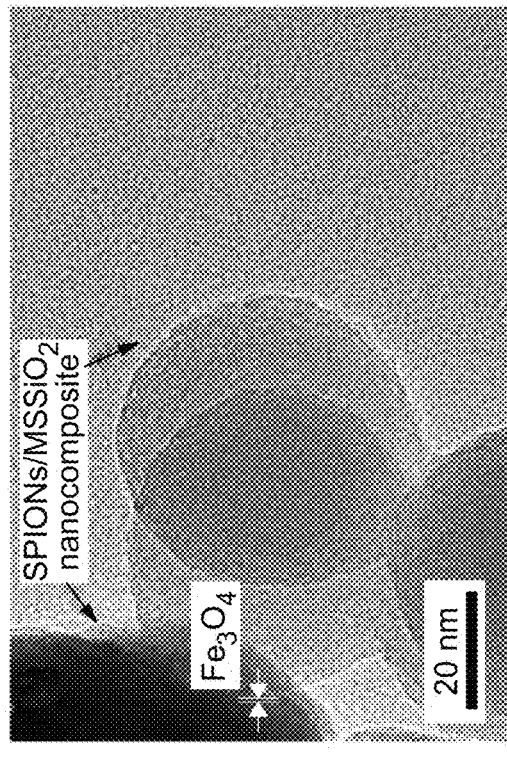
FIG. 3A
FIG. 3B
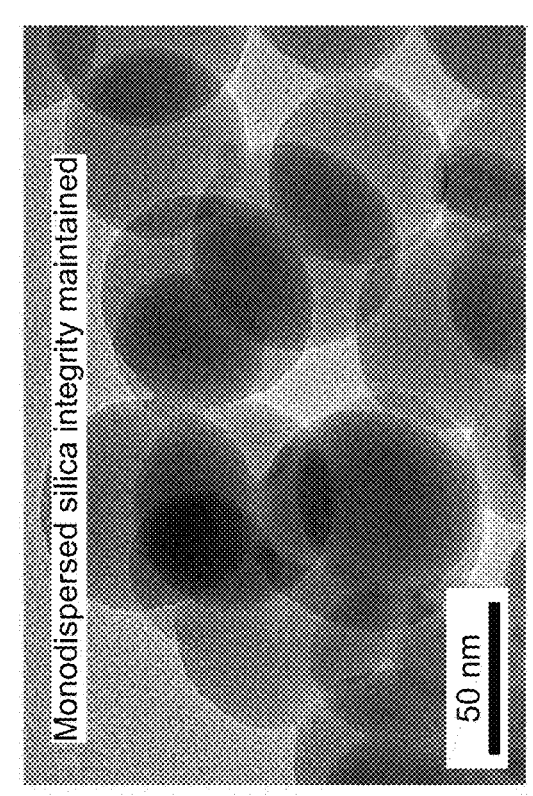
FIG. 3C
FIG. 3D

METHOD OF TREATING COVID-19 INFECTION USING SUPERPARAMAGNETIC IRON OXIDE NANOPARTICLE

STATEMENT OF ACKNOWLEDGEMENT

The Authors extend their appreciation to Deputyship for Research & Innovation, Ministry of Education in Saudi Arabia, under grant number Covid19-2020-004-IRMC, for funding this research work.

BACKGROUND

Technical Field

The present disclosure is directed to superparamagnetic iron oxide nanoparticles, and particularly to a method of treating covid-19 infection using the superparamagnetic iron oxide nanoparticles.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Coronavirus disease (COVID-19) is caused by the severe acute respiratory syndrome coronavirus 2 (SARS-COV-2). The genomic sequence analysis of SARS-COV-2 revealed that the virus contains spike proteins, a receptor binding domain (RBD) that is used to hold the host cells, and a cleavage site used to crack open and enter the host cells. The proteins effectively target the receptor termed as angiotensin-converting enzyme (ACE-2) that is involved in maintaining blood pressure. The angiotensin system has been reported to play a role in cardiovascular homeostasis, acute inflammation, and autoimmune disorders. Further, cancer has been reported to increase viral infection and thereby those with cancer are more prone to SARS-COV-2 infection.

Several antiviral drugs like dexamethasone, favipiravir, ribavirin, interferons, hydroxychloroquine combined with antibiotic azimethrone, lopinavir/ritonavir in combination with interferon, were found to be effective in the treatment of COVID-19. However, poor gastrointestinal stability, low bioavailability, poor transport behavior, and side effects on other organs like the kidneys, limit their therapeutic effectivity. The delivery of drugs to a particular site, such as the pulmonary system, as it forms the main site for SARS-COV-2 invasion, is important to circumvent poor absorption and low bioavailability of the drugs. Recently, studies have shown promising results for pulmonary delivery with nanostructured carriers.

Nanobiotechnology research has risen for developing targeted drug delivery systems. The ability of nanoparticles to accommodate several components into a nanostructure allow for a delivery system with a multifunctional modality. Several nanocarriers based on liposomes, micelles, and polymers conjugated with drugs and dendrimers have been reported for treating pulmonary infections. Further, incorporation of magnetic nanosilica into the drug carrier allows for a response to an external magnetic field, thereby assisting bioimaging, magnetic targeting agent, and carrying a drug for targeted delivery. Hence, there is need for a drug delivery system to improve treatment efficacy and increase site-specific drug delivery. Therefore, it is one object of the present disclosure to describe a method of treating a COVID-19 infection with a magnetic, targeted, and biocompatible composition.

SUMMARY

In an exemplary embodiment, a method of treating a COVID-19 infection is described. The method of treating the COVID-19 infection includes administering to a subject in need thereof an effective amount of a composition, where the composition includes silica nanoparticles, superparamagnetic iron oxide nanoparticles (SPIONs), chitosan, cisplatin, ribavirin, and an angiotensin-converting enzyme 2 (ACE-2). The SPIONs and ACE-2 are dispersed on an outer surface of the silica nanoparticles. The chitosan at least partially wraps around the outer surface of the silica nanoparticles. The cisplatin and ribavirin are in pores of the silica nanoparticles. The particles of the composition are monodisperse, and spherical, and have an average diameter of 70-100 nanometers (nm).

In some embodiments, the composition includes 0.01-10 weight percentage (wt. %) of the ribavirin, based on a total weight of the composition.

In some embodiments, the composition includes 0.01-10 wt. % of the cisplatin, based on the total weight of the composition.

In some embodiments, the composition includes 5-20 wt. % of the SPIONs, based on the total weight of the SPIONs and silica nanoparticles.

In some embodiments, the composition has a Brunauer-Emmett-Teller (BET) surface area of 50-100 square meters per gram ($m^2/g$).

In some embodiments, the composition has an average pore size of 10-20 nm.

In some embodiments, the composition has an average pore volume of 0.25-0.35 cubic centimeters per gram ($cm^3/g$).

In some embodiments, the SPIONs are spherical and have an average diameter of 50-100 nm.

In some embodiments, the SPIONs are aggregated with an average aggregate size of 200-500 nm.

In some embodiments, the composition has a saturation magnetization value of 8-9 electromagnetic units per gram (emu/g).

In some embodiments, the chitosan is hydrogen bonded to the outer surface of the silica nanoparticles.

In some embodiments, the chitosan only wraps around an external pore wall of the silica nanoparticles and does not block the pores of the silica nanoparticles.

In some embodiments, after 72 hours of administering, the composition releases 20-30% of the cisplatin at a pH of 5-6.

In some embodiments, after 72 hours administering, the composition releases 10-20% of the ribavirin at a pH of 5-6.

In some embodiments, after 72 hours administering, the composition releases less than 15% of the cisplatin at a pH of 7-8.

In some embodiments, after 72 hours administering, the composition releases less than 5% of the ribavirin at a pH of 7-8.

In some embodiments, the method includes exposing the subject to an alternating magnetic field in a vicinity of a lung of the subject after administering the composition.

In some embodiments, the method includes following the administering the composition is internalized by at least one lung cell.

The foregoing general description of the illustrative present disclosure and the following The detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 3A shows a transmission electron microscope (TEM) image of SPIONs/$MSSiO_2$, according to certain embodiments;

FIG. 3B shows a TEM image of SPIONs/$MSSiO_2$, according to certain embodiments;

FIG. 3C shows a TEM image of SPIONs/$MSSiO_2$/Chi/ ribavirin (Rib)/Cp. according to certain embodiments;

FIG. 3D shows a TEM image of SPIONs/$MSSiO_2$/Chi/ Rib/Cp, according to certain embodiments;

DETAILED DESCRIPTION

Figure 1A:
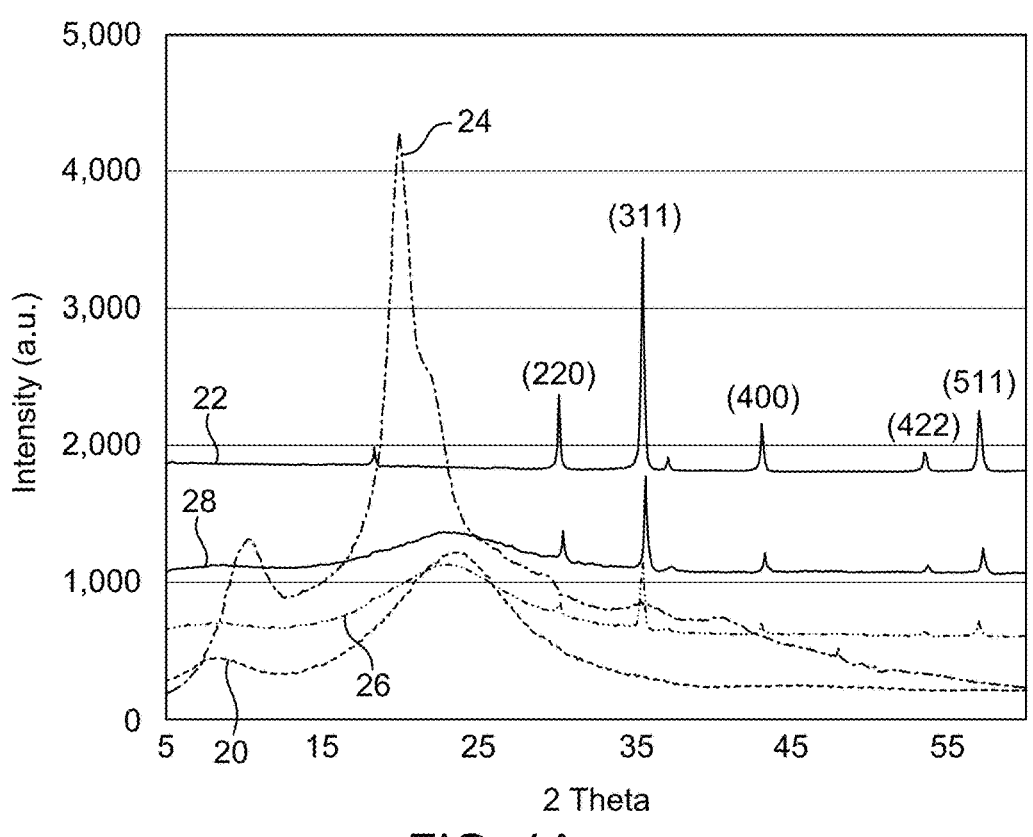
FIG. 1A shows an X-Ray Diffraction (XRD) pattern of silica ($MSSiO_2$) (20), superparamagnetic iron oxide nanoparticles (SPIONs) (22), chitosan (Chi) (24), SPIONs/$MSSiO_2$ (26) and SPIONs/$MSSiO_2$/Chi (28), according to certain embodiments.

In the drawings, reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Where a numerical limit or range is stated herein, the endpoints are included. Also, all values and subranges within a numerical limit or range are specifically included as if explicitly written out.

Aspects of the present disclosure are directed to a method of treating a coronavirus disease (COVID-19) infection. The method includes site specific delivery of a composition including both an anticancer drug and an antiviral drug to the pulmonary system.

The order in which the method is described is not intended to be construed as a limitation, and any number of the described method steps can be combined in any order to implement the method. Additionally, individual steps may be removed or skipped from the method without departing from the spirit and scope of the present disclosure.

The method of treating the COVID-19 infection includes administering to a subject in need thereof an effective amount of a composition. The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human. As used herein, a subject in need of therapy includes a subject already with the disease, a subject which does not yet experience or exhibit symptoms of the disease, and a subject predisposed to the disease. In preferred embodiments, the subject has a COVID-19 infection. In more preferred embodiments, the subject has a COVID-19 infection and cancer. In some embodiments, the cancer is selected from the group consisting of testicular, ovarian, bladder, head and neck, lung and cervical cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and rectal administration. Those of ordinary skill in the art are familiar with administration techniques that can be employed with the compounds and methods described herein.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the composition being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg, preferably 1-25 g/kg, 5-20 g/kg, or 10-15 g/kg of the composition per body weight of the subject.

In some embodiments, the composition includes silica, superparamagnetic iron oxide nanoparticles (SPIONs), chitosan, cisplatin, ribavirin, and an angiotensin-converting enzyme 2 (ACE-2). In some embodiments, the silica acts as a porous silicate matrix that transports the other incorporated materials to the desired site. In general, any suitable porous silicate matrix known to one of ordinary skill in the art may be used in the composition. Examples of such suitable porous silica, silicate, or aluminosilicate materials include, but are not limited to, MCM-41, MCM-48, Q-10 silica, hydrophobic silica, mesobeta, mesoZSM-5, SBA-15, KIT-5, KIT-6, mesosilicalite, hierarchical porous silicalite, and SBA-16. For the purposes of this disclosure, "silicate matrix" also includes aluminum-containing silicate materials. Such materials may be known as or referred to as aluminosilicates. Further, the term "silicate matrix" should be understood to include silica itself. Methods of obtaining the various types porous silica, silicate, or aluminosilicate material are well-known in the art [see for example Gobin, Oliver Christian "SBA-16 Materials: Synthesis, Diffusion, and Sorption Properties" Dissertation, Laval University, Ste-Foy, Quebec, Canada, January 2006, in particular section 2.2; and U.S. patent application Ser. No. 15/478,794—both incorporated herein by reference in their entireties].

In a preferred embodiments, the porous silicate matrix is silica nanoparticles. In general, the nanoparticles can be any shape known to one of ordinary skill in the art. Examples of suitable shapes the nanoparticles may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplates, nanodisks, rods (also known as nanorods), and mixtures thereof. In some embodiments, the nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of nanoparticles having a different shape. As used herein, the term "non-uniform shape" refers to an average consistent shape that differs by more than 10% of the distribution of nanoparticles having a different shape.

In a preferred embodiment, the silica nanoparticles are in the form of spheres. In some embodiments, the sphere has an average diameter of 60-100 nm, preferably 65-95 nm, 70-90 nm, 75-85 nm, or about 80 nm. In a preferred embodiment, the silica nanoparticles are monodisperse, for example the nanoparticles do not vary in size by more than +10%, preferably 5%, or 2%. In an embodiments, the silica nanoparticles have a surface area of 150-200 $m^2$/g, preferably 160-190 $m^2$/g, or 170-180 $m^2$/g. In an embodiments, the silica nanoparticles have a pore volume of 0.3-0.4 $cm^3$/g, preferably 0.32-0.38 $cm^3$/g, 0.34-0.36 $cm^3$/g, or about 0.35 $cm^3$/g. In an embodiments, the silica nanoparticles have a pore diameter of 5-10 nm, preferably 5.5-9.5 nm, 6-9 nm, 6.5-8.5 nm, 7-8 nm, or about 7.5 nm. In an embodiments, the silica nanoparticles have only mesopores (2-50 nm) and no micropores (less than 2 nm).

In some embodiments, the porous silicate matrix is present in an amount of 55 to 85 wt %, preferably 57.5 to 82.5 wt %, preferably 60 to 80 wt %, preferably 62.5 to 77.5 wt %, preferably 65 to 75 wt %, preferably 67.5 to 72.5 wt %, preferably 69 to 71 wt %, preferably 70 wt %, based on a total weight of the composition.

The composition further includes SPIONs. SPIONs are preferably iron oxide ($Fe_3O_4$) nanoparticles. They are well-known in the art and can be obtained by various methods, see for example U.S. Pat. Nos. 9,161,996 and 8,962,031—both incorporated herein by reference in their entirety, and Szpak et al. ["Stable aqueous dispersion of supermagnetic iron oxide nanoparticles protected by charged chitosan derivatives" J. Nanopart. Res (2013) 15 (1), 1372—incorporated herein by reference in its entirety]. In some embodiments, the SPIONs are co-doped and have a magnetic ferrite of formula $MFe_2O_4$ where M is at least one transition metal selected from the group consisting of Cu, Ni, Co, and Mn. In some embodiments, the magnetic ferrite is a mixed metal or doped metal ferrite of formula $M_{1-x}A_xFe_2O_4$, where A represents a transition metal or rare earth element and $0<x\leq0.5$. Examples of such mixed meal or doped metal ferrites include $Mn_{0.5}Zn_{0.5}Fe_2O_4$. In a preferred embodiment, the SPIONs consist of $Fe_3O_4$.

In general, the SPIONs can be any shape known to one of ordinary skill in the art. Examples of suitable shapes the SPIONs may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplates, nanodisks, rods (also known as nanorods), and mixtures thereof. In some embodiments, the SPIONs are spherical and have an average diameter in the range of 1 to 100 nm, preferably in the range of 10 to 90 nm, 20 to 80 nm, 30 to 70 nm, 40 to 60 nm, or about 50 nm.

The SPIONs are loaded on the silica in an amount in the range of 1 wt. % to 20 wt. %, preferably in the range 3 wt. % to 18 wt. %, more preferably in the range of 5 wt. % to 15 wt. %, and most preferably in the range of 8 wt. % to 12 wt. % of the total weight the SPIONs and silica. In a particularly preferred embodiment, SPIONs are loaded on the silica in an amount of about 10 wt. % of the total weight the SPIONs and silica.

Figure 7:
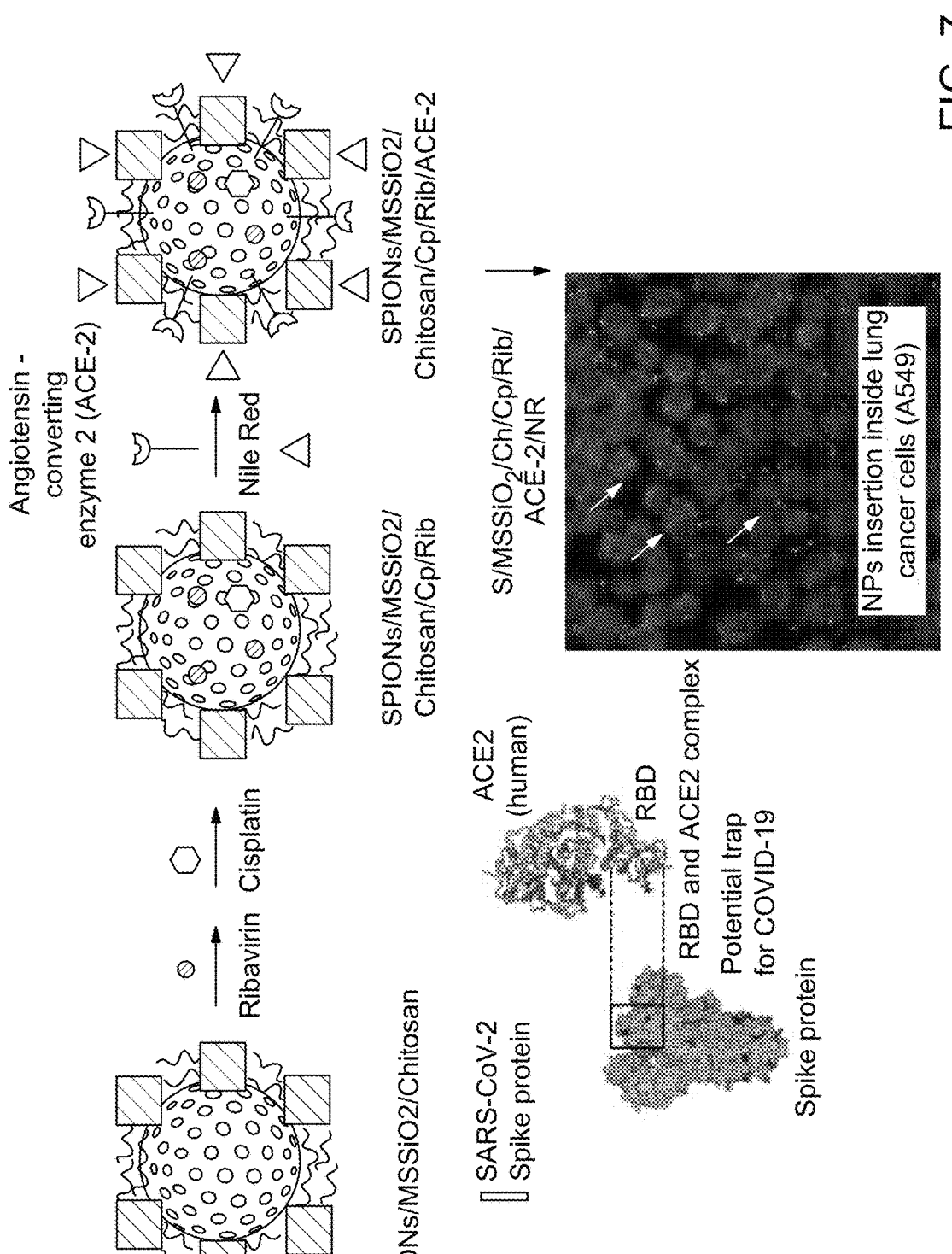
FIG. 7 shows the fabrication of magnetic/monodispersed spherical silica loaded with antiviral/anticancer drugs, angiotensin-converting enzyme 2 (ACE-2) protein, and Nile red dye for potential anticancer and COVID-19-related antiviral treatment, according to certain embodiments.

In some embodiments, the SPIONs are dispersed on an outer surface of the silica nanoparticles. An embodiment of the SPIONs on the outer surface is depicted in FIG. 7, where the SPIONs are represented by the square shapes. In a preferred embodiment, the SPIONs do not penetrate a pore of the silica. In some embodiments, the addition of SPIONs reduces the surface area and pore volume as it blocks some of the openings, resulting in a surface area of 100-150 m$^2$/g, preferably 110-140 m$^2$/g, or 120-130 m$^2$/g, and a pore volume of 0.25-0.35 cm$^3$/g, preferably 0.27-0.33 cm$^3$/g, 0.29-0.31 cm$^3$/g, or about 0.30 cm$^3$/g. In some embodiments, the SPIONs are aggregated on the outer surface of the silica with an average aggregate size of 200-500 nm. In a preferred embodiment, the aggregates comprise 1-10 SPIONs, preferably 2-9, 3-8, 4-7, or 5-6 SPIONs. In a preferred embodiment, the aggregates do not exceed 5 SPIONs.

In some embodiments, the composition further comprises a biocompatible coating. Such a biocompatible coating may be disposed upon the nanocarrier and/or the pharmaceutical agent mixture. In general, the biocompatible coating may be any suitable coating known to one of ordinary skill in the art. Examples of such suitable biocompatible coatings include, but are not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly (lactic/glycolic acid), cellulose, a cellulose derivative, a glycol, polylactide-polyglycolide, polymethyldisiloxane, polycaprolactone, polylactic acid, and ethylene vinyl acetate. In a preferred embodiment, the composition further includes chitosan.

The chitosan may have a Mw in a range of from 30 to 250 kDa, e.g., at least 35, 40, 45, 50, 55, 60 65, 70, 75, 80, 85, 90, 95, 100, 125, or 150 kDa and/or up to 250, 225, 200, 190, 180, 175, 170, 165, 160, 155, 150, 145, 140, 135, 130, or 125 kDa. The degree of acetylation of the chitosan may be, e.g., at least 5, 6, 7, 8, 9, 10, 12.5, or 15% and/or up to 50, 45, 40, 35, 32.5, 30, 27.5, 25, 22.5, 20, 19, 18, 17.5, 17, 16, 15, 14, 13, 12.5, 12, 11, or 10%, whereby degrees of acetylation beyond 20% may be from reacetylated forms of chitosan/ chitin, which retain sufficient solubility to be coated onto the silica. The chitosan may constitute no more than 10, 9, 8, 7, 6, 5, 4, 3, 2, 1, or 0.5 wt. % of total composition weight. In a preferred embodiment, the chitosan is 0.1-1 wt. % of the total composition weight, preferably 0.2-0.9 wt. %, 0.3-0.8 wt. %, 0.4-0.7 wt. %, or 0.5-0.6 wt. %.

In an embodiment, the chitosan at least partially wraps around the outer surface of the silica nanoparticles. An embodiment of the chitosan on the outer surface is depicted in FIG. 7, where the chitosan are represented by the wavy lines. In a preferred embodiment, the chitosan does not penetrate a pore of the silica. In a preferred embodiment, the chitosan wraps around at least 5%, preferably 10%, 15%, 20%, 30%, 40%, 50%, 60%, 70%, 80%, 90%, or 100% of the silica. The chitosan is typically added after the SPIONs are therefore SPIONs are also coated with the chitosan. In some embodiments, the chitosan is hydrogen bonded to the outer surface of the silica nanoparticles. In some embodiments, the chitosan only wraps around an external pore wall of the silica nanoparticles and does not block the pores of the silica nanoparticles. As the chitosan is hydrogen bonded to the silica, these interactions occur around the pores.

In some embodiments, the composition further comprises an anticancer drug. Exemplary anticancer drugs include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; antimicrotubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

In preferred embodiments, the anticancer drug is a platinum (II) complex effective for the treatment of cancer. Many platinum (II) complexes effective for treatment of cancer are well-known in the art including. Any platinum (II) complexes effective for treatment of cancer can be used as the drug treatment agent of the composition including, but not limited to, cisplatin, carboplatin, oxaliplatin, nedaplatin, triplatin tetranitrate, phenanthriplatin, picoplatin, stratapla-tin or mixtures thereof. In a preferred embodiment, the platinum (II) complex is at least one of cisplatin, carboplatin, oxaliplatin, and nedaplatin. In some embodiments, the composition includes 0.01-10 wt. % of the one or more platinum (II) complexes, based on the total weight of the composition, preferably 0.1-9 wt. %, 1-8 wt. %, 2-7 wt. %, 3-6 wt. %, or 4-5 wt. %.

In some embodiments, the composition further comprises an antiviral drug. In particular the antiviral drug is for treating a COVID-19 infection. The antiviral drug is any antiviral drug known in the art to treat a COVID-19 infection. In a preferred embodiment, the antiviral drug is ribavirin. Ribavirin is an antiviral medication used to treat respiratory syncytial virus (RSV) infection, hepatitis C, and some viral hemorrhagic fevers. In some embodiments, the composition includes 0.01-10 wt. % of the antiviral drug, based on the total weight of the composition, preferably 0.1-9 wt. %, 1-8 wt. %, 2-7 wt. %, 3-6 wt. %, or 4-5 wt. %.

In some embodiments, the anticancer drug and antiviral drug are in pores of the silica nanoparticles. In preferred embodiments, the cisplatin and ribavirin are in pores of the silica nanoparticles. Following administration to the subject, the cisplatin and ribavirin are released from the silica pores in the site specific location, as will be described later.

In some embodiments, the composition further comprises angiotensin-converting enzyme 2 (ACE-2). The ACE-2 are dispersed on an outer surface of the silica nanoparticles. In a preferred embodiment, the ACE-2 is not in the pores of the silica. While not wishing to be bound to a single theory, it is thought that as the SARS-CoV-2 spike proteins target ACE-2, incorporating ACE-2 into the composition will trick the virus into targeting the composition. This allows for the composition to then release the antiviral and anticancer drugs to combat the viral infection and cancer. In a preferred embodiment, the ACE-2 is 0.01-1 wt. % of the total composition weight, preferably 0.05-0.8 wt. %, 0.1-0.6 wt. %, 0.2-0.4 wt. %, or about 0.3 wt. %.

In the composition including silica, SPIONs, chitosan, cisplatin, ribavirin, and ACE-2, the particles maintain the shape and size of the original silica particles. In a preferred embodiment, the composition particles are monodisperse, and spherical, and have an average diameter of 70-100 nm, preferably 75-95 nm, 80-90 nm, or about 85 nm. In some embodiments, the composition has a Brunauer-Emmett- Teller (BET) surface area of 50-100 m$^2$/g, preferably 60-90 m$^2$/g, or 70-80 m$^2$/g. In an embodiments, the composition has a pore volume of 0.25-0.35 cm$^3$/g, preferably 0.27-0.33 cm$^3$/g, 0.29-0.31 cm$^3$/g, or about 0.30 cm$^3$/g. In an embodiments, the composition has a pore diameter of 10-20 nm, preferably 12-18 nm, 13-17 nm, 14-16 nm, or about 15 nm. In some embodiments, 30-60% of the surface area of the silica nanoparticles is covered with the other components of the composition, preferably 35-55%, of 40-50%.

Following the administering, the composition releases the antiviral and anticancer drugs from the pores into the subject. In some embodiments, after 72 hours of administering, the composition releases 20-30%, preferably 22-28%, 24-26% or approximately 25% of the cisplatin at a pH of 5-6, preferably 5.1, 5.2, 5.3, 5.4, 5.5, 5.6, 5.7, 5.8, 5.9, or 6.0. In some embodiments, after 72 hours administering, the composition releases 10-20%, preferably 12-18%, 14-16%, or about 15% of the ribavirin at a pH of 5-6, preferably 5.1, 5.2, 5.3, 5.4, 5.5, 5.6, 5.7, 5.8, 5.9, or 6.0. In some embodiments, after 72 hours administering, the composition releases less than 15%, preferably 10%, 5%, or 0% of the cisplatin at a pH of 7-8, preferably 7.1, 7.2, 7.3, 7.4, 7.5, 7.6, 7.7, 7.8, 7.9, or 8.0. In some embodiments, after 72 hours administering, the composition releases less than 5%, preferably 4%, 3%, 2%, 1%, or 0% of the ribavirin at a pH of 7-8, preferably 7.1, 7.2, 7.3, 7.4, 7.5, 7.6, 7.7, 7.8, 7.9, or 8.0.

It is known that COVID-19 interacts with cells at a pH of 5.5. Therefore, release of the drugs from the composition near this pH (5-6) is preferable. Further, release of the drugs outside of the pH range is not preferred. Unexpectedly, the composition releases a higher amount of the antiviral and anticancer drugs in the pH range of 5-6 compared to that of the range of 7-8 (normal physiological conditions). Therefore, the composition is suitable as a treatment for a COVID-19 infection and can be considered a pH responsive composition.

The presence of the particles of a SPIONs in the composition may serve one or more purposes. A first purpose may be to aid targeting the drug to a particular diseased tissue by applying external magnetic field to the diseased tissues, and thereby concentrating the drug in the diseased tissues in need of treatment and minimize the drug contacts with healthy tissues. A second purpose may be that the particles of a magnetic ferrite are magnetic contrasting agent used in magnetic resonance (MM) imaging. Thus, the method of treatment may involve a combination of administering effective amount of the drug to a subject, while observing and targeting the drug to the diseased tissue by an applied external magnetic field. A third purpose may be that the particles of a magnetic ferrite may be used in magnetic heating. Such heating is a response to exposure of the nanocarrier to an alternating magnetic field. Such heating may be useful for a purpose such as increasing the rate of anticancer and/or antiviral drug release, increasing the amount of anticancer and/or antiviral drug released, and/or hyperthermia treatment of cancer. Hyperthermia treatment is a treatment method which involves heating a tissue, tumor, or other area to a temperature above its normal temperature. Such heating may be achieved by the application of an alternating magnetic field to a magnetic material co-located with the desired treatment area, laser heating, microwave heating, or any other suitable heating method known to one of ordinary skill in the art. In some embodiments, the method further comprises exposing the subject to an alternating magnetic field, thereby raising the temperature of the composition.

In some embodiments, the method further includes exposing the subject to an alternating magnetic field in a vicinity of a lung of the subject after administering the composition. In some embodiments, the composition has a saturation magnetization value of 8-9 electromagnetic units per gram (emu/g), preferably 8.2-8.8 emu/g, 8.4-8.6 emu/g or about 8.5 emu/g. In an embodiment, the composition is superparamagnetic and not ferromagnetic. Thus, exposing the subject to an alternating magnetic field in a vicinity of a lung of the subject after administering the composition, draws the composition based on its superparamagnetic properties to the desired location, i.e. the lung.

In some embodiments, the method includes following the administering the composition is internalized by at least one lung cell. While not wishing to be bound to a single theory, it is thought that the small size of the composition particles allows for passage of the composition into the tracheal mucus region of the subject's lungs, and then the ACE-2 receptor binds with the lung cells which then internalize the composition. Therefore, if the SARS-COV-2 were to attack the cell with the internalized composition, the antiviral and anticancer drugs are present to combat the infection.

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GPSd, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HRS, and C-41, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, cervical cancer, testicular cancer, and/or breast cancer.

The composition may further comprise one or more pharmaceutically acceptable carriers. As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a pharmaceutical composition will depend upon the intended route of administration for the pharmaceutical composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween® 20), polysorbate 60 (Tween® 60), and polysorbate 80 (Tween® 80), cationic surfactants, e.g., decyltrimethylammonium bromide, bromide, dodecyltrimethyl ammonium tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as gels, pastes, and suppositories, liquid dosage forms such as suspension, and dispersions, inhalation dosage form such as aerosols, sprays, and powders.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection dispersions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These dispersions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal cancer, but may be unsuitable for treating other cancers.

In a preferable embodiment of the invention, the composition is administered through a nasal or oral passage of a subject. Administration by inhalation is preferable to direct the composition to the lungs of the subject. Preferably the composition is administered as a dry powder, such as a dry aerosol, which comprises and/or consists of the composition. The aerosol is formed by suspending the dry composition in a gaseous (e.g., air) fluid stream. The thus fluidized dry powder is confined to a delivery container in which the gaseous stream is recirculated. Administration of the composition to the subject is then accomplished by diverting the aerosol stream from a recirculation mode in the container to a delivery mode such that a controlled volume of fluidized material is dispensed from the container. When delivered in this manner, into a nasal or oral passage of the subject, the composition is deposited on a surface of the tracheal mucus region. Administration in an aerosolized form permits deposition of a uniform layer of the composition on a controlled surface area of the subject's tracheal mucosal region.

EXAMPLES

The following examples demonstrate a method of treating coronavirus disease (COVID-19) infection using superparamagnetic iron oxide nanoparticles (SPIONs), as described herein. The examples are provided solely for illustration and are not to be construed as limitations of the present disclosure, as many variations thereof are possible without departing from the spirit and scope of the present disclosure.

Example 1: Materials

Superparamagnetic iron oxide nanoparticles (SPIONs) ($Fe_3O_4$, 97%) with particle size between 50-100 nm and Halloysite nanotubes (Hal) were purchased from Sigma Aldrich, 3050 Spruce St Saint Louis, MO, 63103-2530, United States of America. The silica nanoparticles (MS-$SiO_2$) in dispersed spherical form were purchased from Superior silica, 5600 Clearfork Main St #400, Fort Worth, TX 76109, USA. Anticancer drug (cisplatin (Cp)), antiviral drug (1-β-D-Ribofuranosyl-1,2,4-triazole-3-carboxamide, ribavirin (Rib)), Angiotensin Converting Enzyme-2 (ACE-2) and chitosan (Chi) were obtained from Sigma Aldrich, 3050 Spruce St Saint Louis, MO, 63103-2530, United States of America. Reagents used to maintain cell cultures were purchased from Thermo-Fisher Scientific, 168 Third Avenue. Waltham, MA USA 02451: DMEM (Dulbecco's Modified Eagle Medium), heat-inactivated fetal bovine serum (HI-FBS), 100× Penicillin Streptomycin, and 100× MEM NEAA (MEM non-essential amino acids). Cell viability assay was performed using the 3-(4,5-dimethylthiazol-2-yl)-2,5-diphenyltetrazolium bromide (MTT) reagent (Thermo-Fisher Scientific, M6494). All reagents are manufactured in a current good manufacturing practice (cGMP)-compliant facility.

Each sample or composition is labeled throughout with abbreviations of each component separated by /. For example, a composition including silica nanoparticles (MS-$SiO_2$), superparamagnetic iron oxide nanoparticles (SPIONs), chitosan (Chi), and ribavirin, would be labeled as SPIONs/MSSiO$_2$/Chi/Rib.

Example 2: Synthesis of SPIONs/MSSiO$_2$/Chi and SPIONs/Hal/Chi Nanocomposites The nanocomposites were prepared using the dry impregnation technique. First, 0.5 grams (g) of SPIONs (10 wt %) were mixed with 5 g of MSSiO$_2$ using mortar and pestle. The black powder was then wrapped with chitosan (0.6 wt/vol %). In the case of S/MSSiO$_2$/Chi, 0.25 g of S/MSSiO$_2$ was added and stirred vigorously in 10 milliliters (ml) of chitosan solution at 800 revolutions per minute (rpm) for 3 hours. The sample was recovered by centrifugation at 14000 rpm for 10 min. Then washed with 5 ml distilled water (DW) three times to remove the physically adsorbed chitosan and dried at 45° C. for 12 hours. SPIONs/Hal/Chi was made by a similar method but with replacing the MSSiO$_2$ with Halloysite nanotubes.

Example 3: Synthesis of SPIONs/MSSiO$_2$/Chi/Cp/Rib and SPIONs/Hal/Chi/Cp/Rib Nanocomposites Cp and Rib were functionalized using normal saline solution (NSS). Initially, 30 mg of Cp and 30 mg of Rib were taken and dissolved in a 10 ml NSS solution. After dissolution, SPIONs/MSSiO$_2$/Chi (600 mg) was added and stirred overnight in an ice bath. Then the sample was recovered through centrifugation at 14000 rpm. Further washed with 5 ml of normal saline solution, the sample was recovered and dried at ambient conditions. Finally, the filtrate was collected for Cp and Rib analysis using ultraviolet (UV)-visible spectroscopy. SPIONs/Hal/Chi/Cp/Rib was made by a similar method but with replacing the MSSiO$_2$ with Halloysite nanotubes.

Example 4: Synthesis of SPIONs/MSSiO$_2$/Chi/Cp/Rib/ACE-2 Nanocomposite

1 μl of ACE-2 receptor was dissolved in 2 ml of normal saline solution and stirred for 10 min. Then 120 mg of SPIONs/MSSiO$_2$/Chi/Cp/Rib and Nile red dye mixture dissolved in 1.5 ml distilled water was added and stirred overnight in an ice bath. Then the mixture was freeze-dried using a lyophilization technique and stored at −20° C.

Example 5: Characterization Techniques

The crystalline and amorphous phases of drugs on nanocarriers were analyzed using X-ray diffraction (XRD) (Miniflex 600, Rigaku, 2601A, Tengda Plaza, No. 168, Xizhimenwai Ave, Japan). The extent of surface occupation and pore changes after drug loadings were measured using the nitrogen adsorption technique (ASAP-2020 plus, Micromeritics, 4356 Communications Dr. Norcross, GA 30093-2901, U.S.A). The chemical environment of SPIONs nanocomposite formation with silica was analyzed using diffuse reflectance spectroscopy (DRS) analysis (JASCO, V-750, 2967-5, Ishikawa-machi, Hachioji, Tokyo 192-8537, Japan). The drug-silica interaction was confirmed using a Fourier transform infrared (FTIR) spectroscopy (L160000A, Perkin Elmer, 940 Winter Street Waltham, MA 02451, USA). The spinel ferrite/halloysite morphology and various elements were analyzed using a scanning electron microscope (SEM) (JSM-6610LV, JEOL, 3-1-2 Musashino, Akishima, Tokyo 196-8558) equipped with energy dispersive spectroscopy (EDS) and transmission electron microscopy (TEM) (FEI, Morgagni 268 at 80 kV, Hillsboro, Oregon, USA).

Example 6: Drug Release Study

The dual release study was performed using a dialysis membrane (Molecular weight cut-off (MWCO)=14,000 Daltons (Da)) technique. Before the study, drugs were calibrated using 5-30 µg/ml concentrations at a specific $\delta_{max}$ of cisplatin and ribavirin. Then, 15 mg of the nano-formulation-containing membrane was placed inside the 25 ml phosphate-buffered saline (PBS) solution at 37° C. The pH of the buffer varied from 5.6 and 7.4, respectively. At specific intervals, 5 ml of solution was withdrawn for analysis while replaced with an equal quantity of fresh PBS solution. The study was conducted in duplicate.

Example 7: Cell Culture and Treatment

To explore the cytotoxic effects of the nanocomposites, a human lung carcinoma cell line (A549) and human embryonic kidney 293 (HEK293) cell line were used. Cells were maintained in DMEM and supplemented with 10% HI-fetal bovine serum (FBS), 1% penicillin-streptomycin, and 1% MEM NEA at 37° C. and 5% carbon dioxide (CO$_2$).

Example 8: Cell Viability (MTT)

96-well plates were used with 20,000 cells/well for the cell viability assay. Cells were treated with nanocomposites for 24 hours after seeding. Treatment conditions were as follows: SPIONs/MSSiO$_2$/Chi (A), SPIONs/Hal/Chi (B), Cp (C), Rib (D), SPIONs/MSSiO$_2$/Chi/Cp (E), SPIONs/Hal/Chi/Cp (F), SPIONs/MSSiO$_2$/Chi/Cp/Rib (G), and SPIONs/Hal/Chi/Cp/Rib (H).

Treatment concentrations for all groups, except Cp (C) and Rib (D), were: 0.025, 0.05, 0.1, and 0.5 mg/ml. According to the drug loading experiment, there were 0.045 mg of Cp and Rib in 1 mg of the nanocomposites. Therefore, the treatment concentrations of free Cp and Rib were: 0.001125, 0.00225, 0.0045, and 0.0225 mg/ml. In other words, if the treatment concentration of the nanocomposite was 0.5 mg/ml, then the treatment concentration for both Cp and Rib should be 0.0025 mg/ml. After 48 hours of treatment, cells were washed, and the MTT solution (0.5 mg/ml) was added to each well for 3 hours at 37° C. After that, the formazan crystals were solubilized with 0.04 normality (N) hydrochloric acid (HCl) isopropyl alcohol. The color change was detected using SYNERGY-neo2 BioTek enzyme-linked immunosorbent assay (ELISA) reader at 570 nm. Each was performed in duplicate (technical repeats) with three experimentally independent biological repeats (n=3). Analysis was performed by comparing each condition with a no-treatment negative control. The percentage viability was calculated using the following formula:

$$\text{Cell Viability } (\%) = (\text{absorbance of treatment}/$$
$$\text{absorbance of negative control}) \times 100.$$

Example 9: Microscopic Examination

To assess the internalization of the nanocomposites, they were functionalized with ACE-2 ligand and Nile Red (NR) dye. The modified nanocomposite was labeled SPIONs/MSSiO$_2$/Chi/Cp/Rib/ACE-2/NR. A549 and HEK293 cells were treated with non-modified and modified conditions (SPIONs/MSSiO$_2$/Chi/Cp/Rib and SPIONs/MSSiO$_2$/Chi/Cp/Rib/ACE-2/NR) at 0.1 mg/ml for 24 hours. Cells were stained with Hoechst 33342 (Thermo-Fisher Scientific, 62249) for 20 min, washed with PBS, and then viewed under the microscope. Zeiss LSM 700 confocal microscope was used to capture the immunofluorescent images.

Example 10: Statistics

The cell viability assay was performed in three experimentally independent biological repeats (n=3). Statistical analysis was performed using Prism 9.2 software (GraphPad, La Jolla, CA). The analysis was performed using two-way ANOVA with Dunnett's post hoc test. Error bars±S.E.M. Statistical significance and p values are listed in Table 2.

Example 11: Characterization of the Nanocomposites

X-ray diffraction (XRD) technique was used to identify the phase (crystalline and amorphous) of SPIONs, loaded drugs, and polymers. FIG. 1A shows an XRD pattern with unique peaks corresponding to silica (MSSiO$_2$) (20), superparamagnetic iron oxide nanoparticles (SPIONs) (22), chitosan (Chi) (24), SPIONs/MSSiO$_2$ (26) and SPIONs/MSSiO$_2$/Chi (28). The spherical silica exhibited a broad characteristic amorphous peak at about 22.5°, while SPIONs showed a highly crystalline peak between 15-60°. Magnetic-silica nanocomposite formation was identified with collective peaks corresponding to spherical silica and crystalline SPIONs (FIG. 1A (20 and 24)). A reduced crystalline peak of SPIONs was observed indexed to (220), (311), (400), (422), (511), and (440) planes (FIG. 1A, (22)). Parent chitosan shows the presence of a broad crystalline peak attributed to hydrogen bonding (inter and intramolecular forces) (FIG. 1A (24)). In the case of SPIONs/MSSiO$_2$/Chi, chitosan wrapping further reduced the peak intensity, indicating chitosan's wrapping over SPIONs/MSSiO$_2$. Similarly, crystalline peaks of chitosan disappear with wrapping over nano-formulations. The high surface area of nanocarriers was thought to improve the multifunctional ability of drugs and proteins.

Figure 1B:
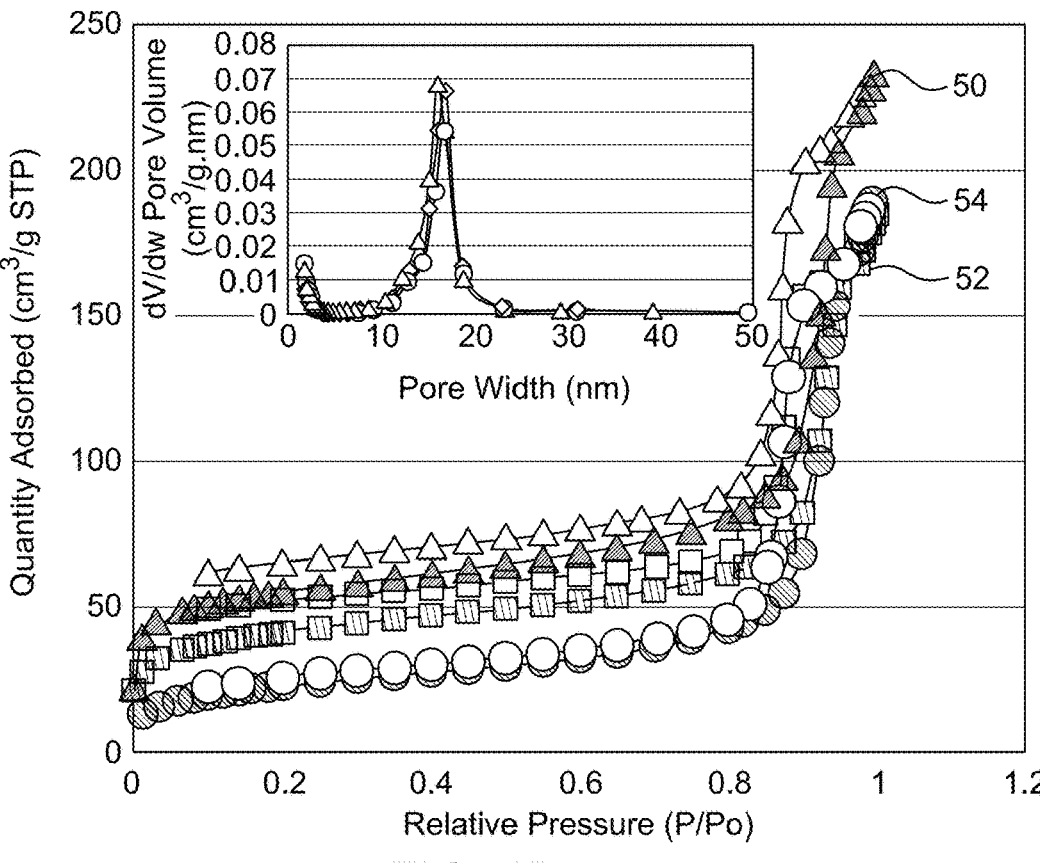
FIG. 1B shows nitrogen adsorption isotherm of the $MSSiO_2$ (50), SPIONs/$MSSiO_2$ (52) and SPIONs/$MSSiO_2$/Chi (54), with an inset showing pore width and volume, according to certain embodiments.

Nitrogen adsorption isotherm was used to determine the textural changes such as surface area and pore characteristics of the nano-formulation. FIG. 1B shows the $N_2$ adsorption isotherm of $MSSiO_2$ (50), SPIONs/$MSSiO_2$ (52) and SPIONs/$MSSiO_2$/Chi (54). Parent $MSSiO_2$ exhibited a type IV isotherm pattern with a high surface area of about 170 $m^2$/g. The pore volume remains at 0.35 $cm^3$/g, while the pore size distribution was about 8.3 nm. In the case of SPIONs/$MSSiO_2$, the surface area reduces to about 130 $m^2$/g indicating the occupation of SPIONs at the external surface of $MSSiO_2$. The pore volume indicates a systematic decrease to 0.28 $cm^3$/g. In the case of the final nano-formulation, a further reduction in surface area to 76 $m^2$/g was observed. The quantity of nitrogen adsorbed decreased, while an increased pore diameter to 15 nm was observed. This showed successful wrapping of chitosan at the SPIONs/$MSSiO_2$, which occurs at the external pore walls of the silica nanoparticles, contributing to increased pore diameter. The results are summarized in Table 1 below.

TABLE 1

The surface area of nanocarrier and nano-formulations.

| Sample | Surface area ($m^2$/g) | Pore volume ($cm^3$/g) | Pore diameter (nm) |
|---|---|---|---|
| $MSSiO_2$ | 170 | 0.35 | 8.3 |
| SPIONs/$MSSiO_2$ | 130 | 0.28 | 8.5 |
| SPIONs/$MSSiO_2$/Chi | 76 | 0.28 | 15 |

Figure 1C:
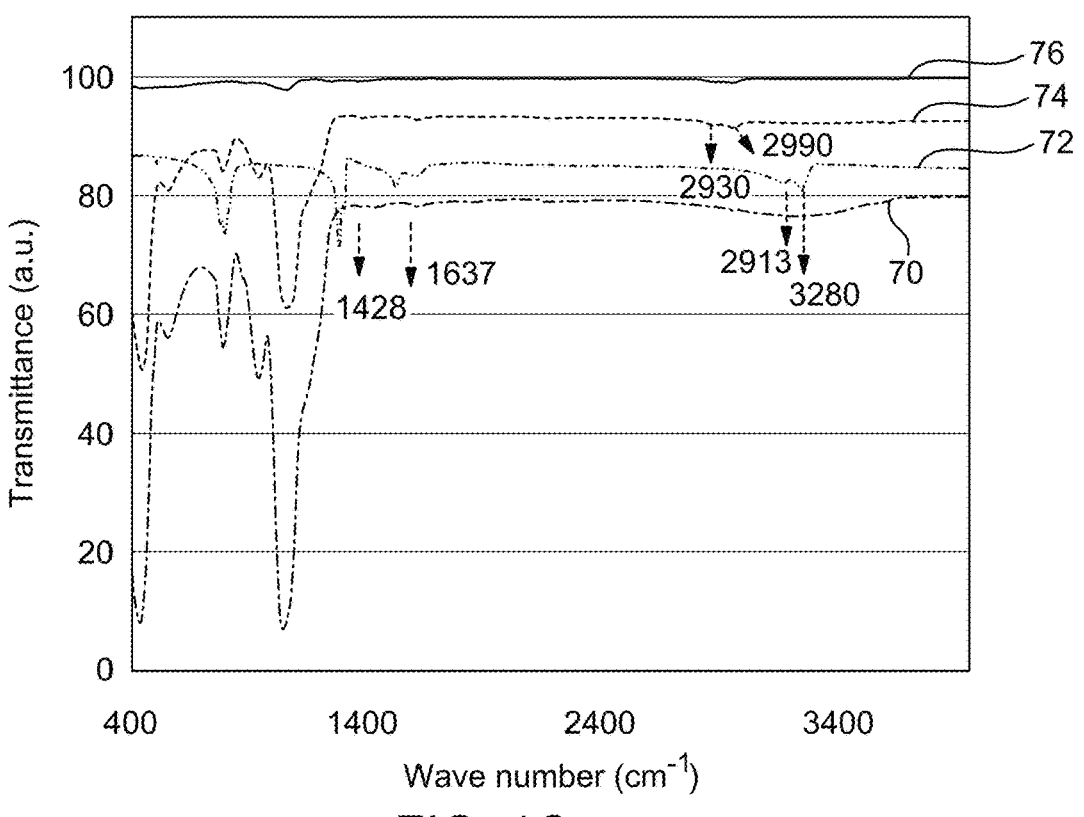
FIG. 1C shows a Fourier transform infrared (FTIR) spectra of the $MSSiO_2$ (70), cisplatin (Cp) (72), chitosan wrapped SPIONs/$MSSiO_2$ (74), and chitosan (76), according to certain embodiments.

The drug/chitosan to nanocarrier interaction was identified using FTIR spectroscopy. FIG. 1C shows the FTIR spectra of $MSSiO_2$ (70), Cp (72), SPIONs/$MSSiO_2$/Chi (74) and Chitosan (76). The $MSSiO_2$, Cp, chitosan-wrapped $MSSiO_2$, and chitosan were analyzed using FTIR. The silica exhibited functional moieties between 2970-3670 $cm^{-1}$ due to OH and NH peaks. Cp showed peaks at 1557 and 3285 $cm^{-1}$. In the case of S/$MSSiO_2$/chitosan, the presence of chitosan peaks at about 2894 and 2998 $cm^{-1}$ signals chitosan wrapping over $MSSiO_2$. The reduction of OH and NH peak at 3275 $cm^{-1}$ confirm the nanocomposite formation with the silica surface.

Figure 1D:
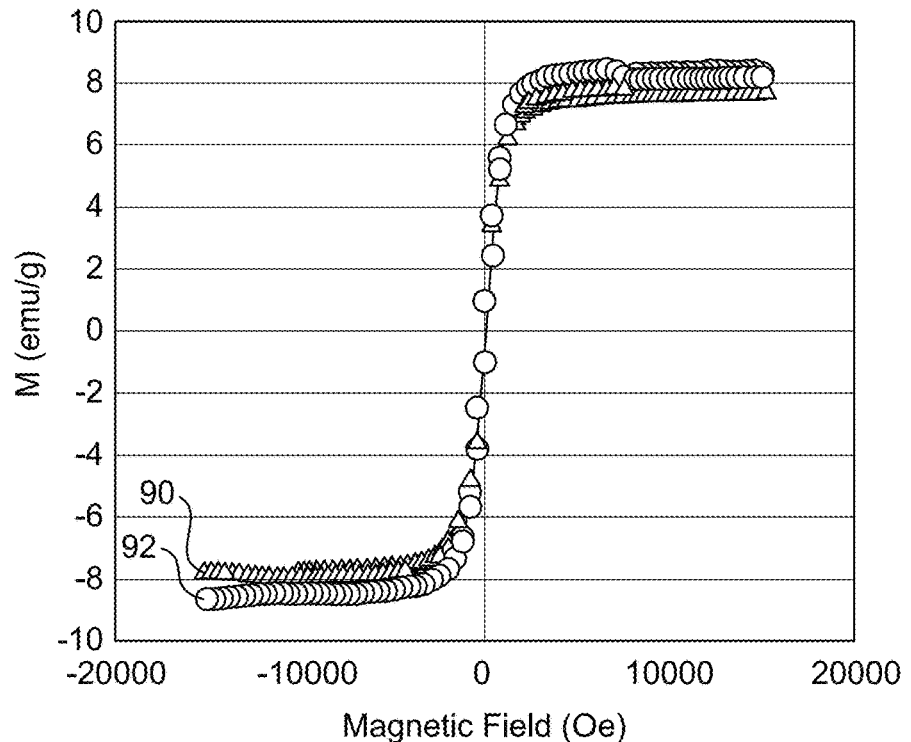
FIG. 1D shows a vibrating sample magnetometer (VSM) analysis of SPIONs/$MSSiO_2$ (90) and SPIONs/Hal (92), according to certain embodiments.

The magnetic property of nano-formulations was measured using a vibrating sample magnetometer (VSM). FIG. 1D shows the VSM of SPIONs/$MSSiO_2$ (90) and SPIONs/Hal (92). Both samples exhibited a superparamagnetic property without a hysteresis loop. The characterization tool reflected the strong magnetic character due to the ferrous-ferric oxide species ($Fe^{2+}$ and $Fe^{3+}$) of $Fe_3O_4$. The observed superparamagnetic characteristics indicated the magnetization of samples and alignment in line with the magnetic field due to $Fe^{2+}$/$Fe^{3+}$ species and interactive dipole-dipole nature. Parent SPIONs were reported to exhibit high magnetization saturation of 67 emu/g. The particle size and nature of the SPIONs nanocluster were reported to influence the magnetic saturation. In the present study, the saturation magnetization value of SPIONs/$MSSiO_2$ and SPIONs/Hal were 8.4 emu/g and 8.2 emu/g, respectively. A reduced magnetic saturation indicates a particle size reduction in nanocomposite formation with $MSSiO_2$ and Hal. It has been reported that small nanoclusters contribute to the superparamagnetic property, while large nanoclusters lead to ferromagnetism [Rabindran, J. B., Vijaya, R., Alamoudi, W. A., Dana, A., Hatim, D., Lina, H. A., Abdulhadi, B., Toprak, M. S. and Thirunavukkarasu, S., 2019. Targeted therapeutic effect against the breast cancer cell line MCF-7 with a $CuFe_2O_4$/silica/cisplatin nanocomposite formulation. Beilstein Journal of Nanotechnology, 10, pp. 2217-2228, incorporated herein by reference in its entirety]. The superparamagnetic behavior indicated the presence of small SPION nanoclusters on the surface of $MSSiO_2$. Further, such non-collinear spin nature at the silica surface allows them to coordinate with an external magnetic field.

Figure 2:
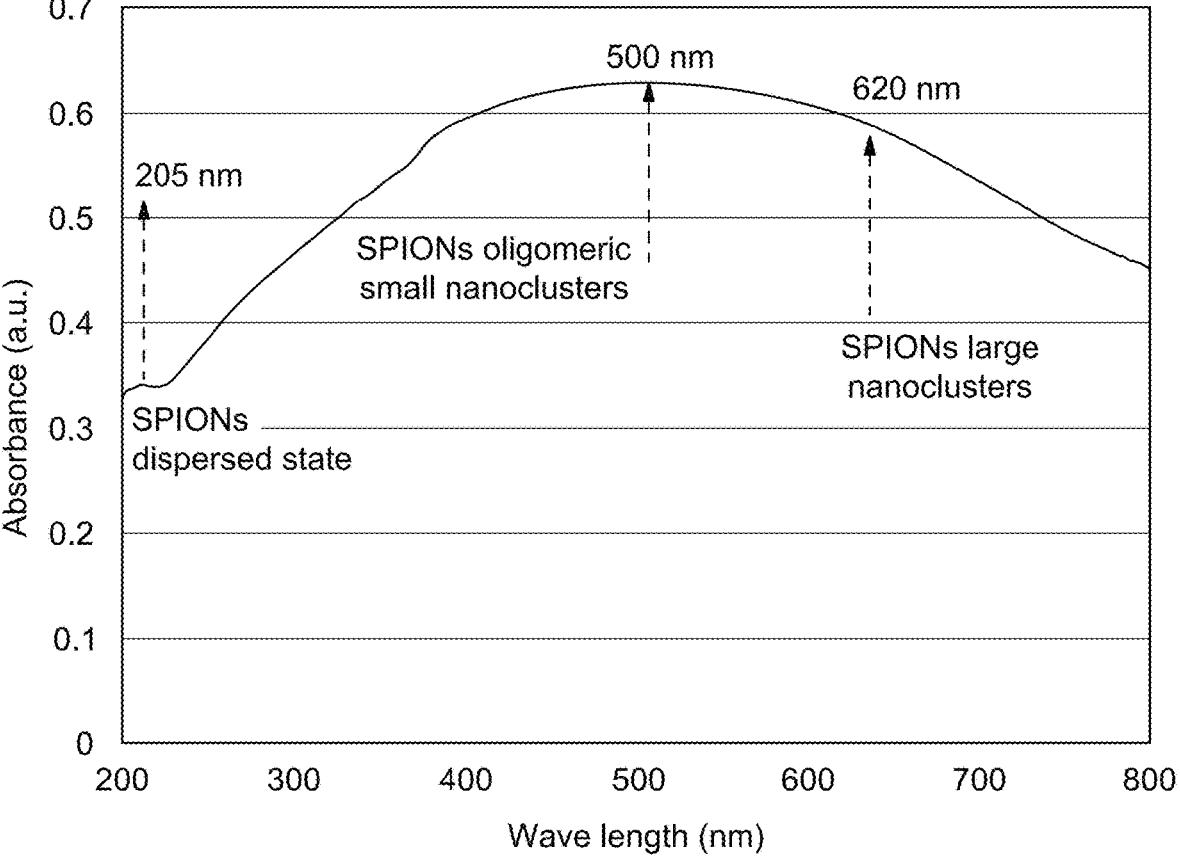
FIG. 2 shows a diffuse reflectance spectrum (DRS) of SPIONs/$MSSiO_2$, according to certain embodiments.

FIG. 2 shows that the coordination of SPIONs on $MSSiO_2$ was investigated using diffuse reflectance spectroscopy. A small absorption peak at about 220 nm showed the tetrahedrally coordinated ferric species ($Fe^{3+}$) in the dispersed state on the $MSSiO_2$ surface. The presence of a band maximum at 500 nm indicated the oligomeric SPIONs nanoclusters, while band expansion above 500 nm signals the presence of larger SPIONs clusters.

FIGS. 3A-3D shows the TEM images of SPIONs/$MSSiO_2$ (FIGS. 3A-3B) and SPIONs/$MSSiO_2$/Chi/Rib/Cp (FIGS. 3C-3D). In SPIONs/$MSSiO_2$, the $MSSiO_2$ particles are spherical and have a diameter of 70-90 nm and form a nanocomposite with the darker colored SPIONs. In SPIONs/$MSSiO_2$/Chi/Rib/Cp, the nanocomposite particles maintains the monodisperse spherical shape and have a diameter of 80-100 nm. This size range allows for drug delivery because nanocarrier particles with sizes between 60-300 nm were reported to diffuse freely in tracheal mucus of mouse.

Example 12: Performance of the Nanocomposites

The drug delivery system nanocomposite should release the drugs (ribavirin and cisplatin) inside of the body of the subject in the targeted are. Also, for effective delivery of the drugs through a pulmonary drug delivery system, the drug should be released at a pH 5.0-6.0, as this is the interactive pH between coronavirus and a cell through the ACE-2 receptor.

Figure 4A:
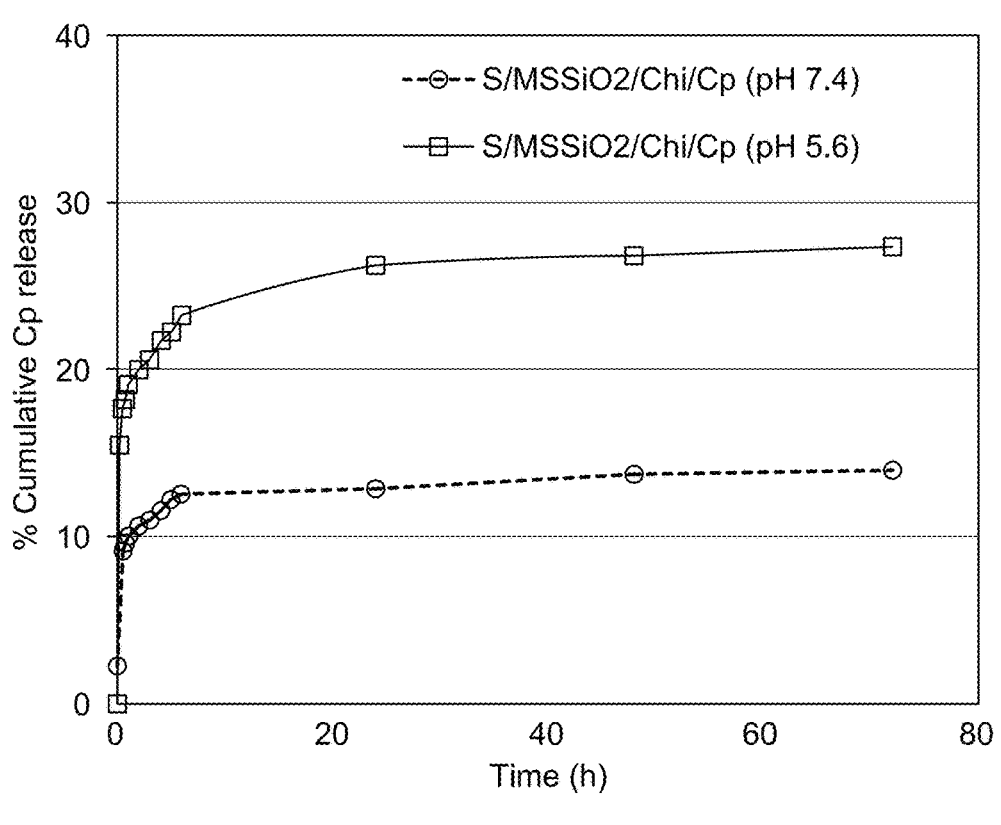
FIG. 4A shows a Cp release profile of SPIONs/$MSSiO_2$/ Chi/Rib/Cp at different pH (7.4 and 5.6 pH), according to certain embodiments.
Figure 4B:
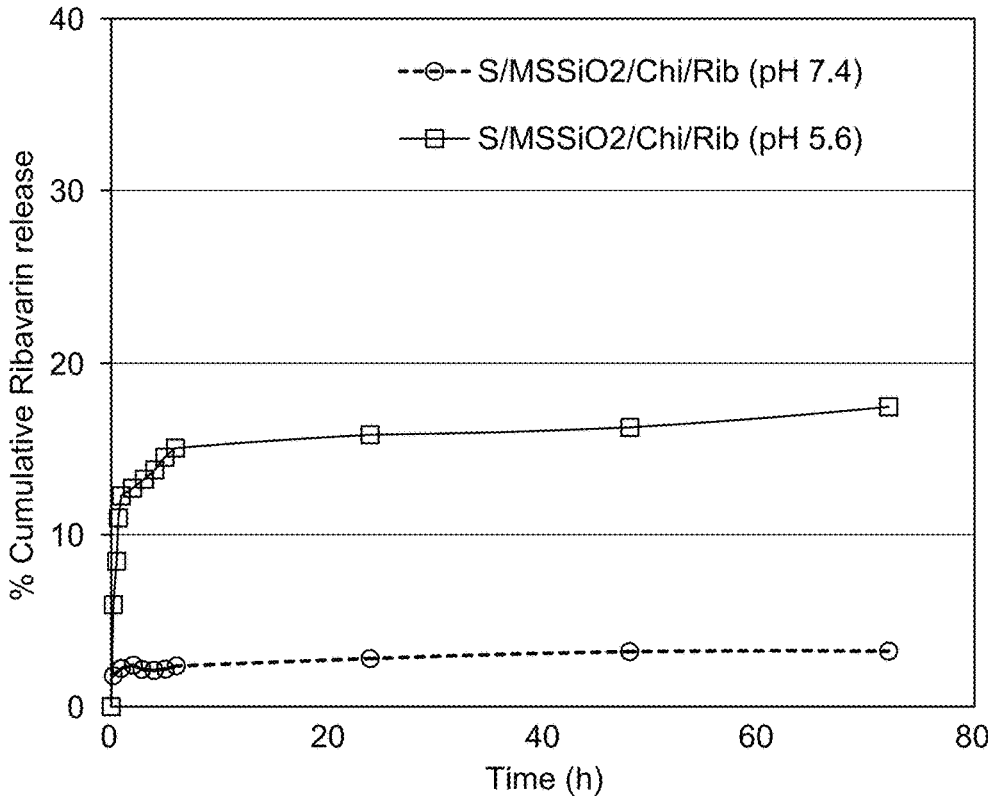
FIG. 4B shows a Rib release profile of SPIONs/$MSSiO_2$/ Chi/Rib/Cp at different pH (7.4 and 5.6 pH), according to certain embodiments.
Figure 4C:
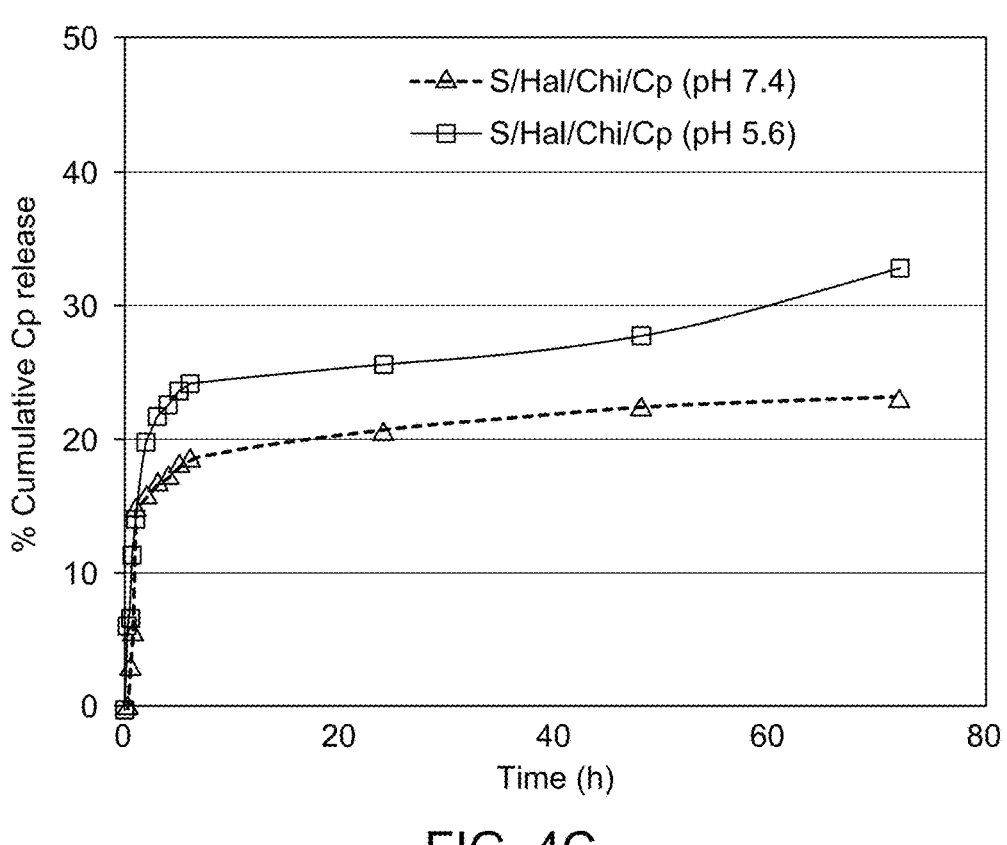
FIG. 4C shows a Cp release profile of SPIONs/halloysite nanotube (Hal)/Chi/Rib/Cp different pH (7.4 and 5.6 pH), according to certain embodiments.
Figure 4D:
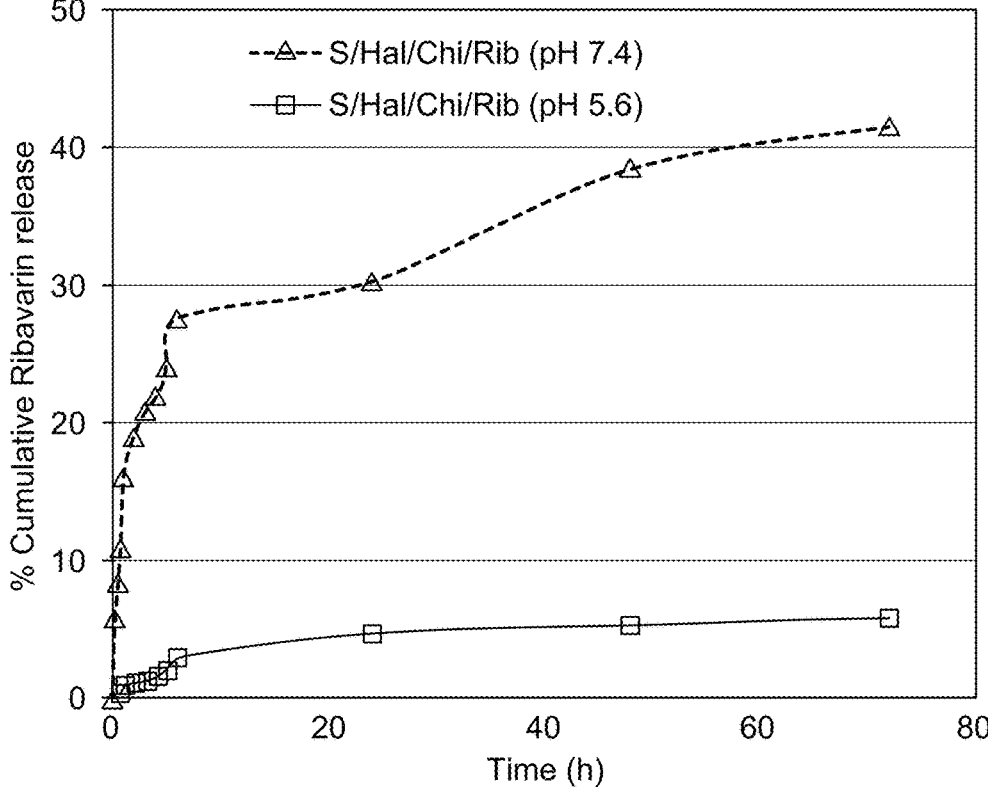
FIG. 4D shows a Rib release profile of SPIONs/Hal/Chi/ Rib/Cp different pH (7.4 and 5.6 pH), according to certain embodiments.

FIG. 4A-FIG. 4D show the antiviral drug ribavirin and anticancer drug cisplatin release capability of SPIONs/$MSSiO_2$/Chi/Rib/Cp and SPIONs/Hal/Chi/Rib/Cp were studied at two pH conditions (pH 5.6 and 7.4) for 72 hours. SPIONs/Hal/Rib/Cp/Chitosan exhibited higher dual drug release than SPIONs/$MSSiO_2$/Rib/Cp/Chitosan. FIG. 4A shows a Cp release profile from SPIONs/$MSSiO_2$/Chi/Cp nano-formulations in 7.4 and 5.6 pH. FIG. 4B shows a Rib release profile with SPIONs/$MSSiO_2$/Chi/Rib nano-formulations in 7.4 and 5.6 pH. FIG. 4C shows a Cp release profile with SPIONs/Hal/Chi/Cp nano-formulations in 7.4 and 5.6 pH. FIG. 4D shows a Rib release profile with SPIONs/Hal/Chi/Rib nano-formulations in 7.4 and 5.6 pH. SPIONs/$MSSiO_2$/Chi/Rib/Cp exhibited a high Cp release of about 27% at pH 5.6, while at normal physiological pH 7.4, the release decreases and reaches 14%. Similarly, the nano-formulation effectively releases ribavirin at pH 5.6 (17%) compared to pH 7.4 (3.2%). The Cp release over SPIONs/Hal/Rib/Cp/Chitosan was highest with 33% at pH 5.6, while reduced to 23% at pH 7.4. The ribavirin release was 41% at pH 5.6 and 6% at pH 7.4. The trend indicates the suitability of both nano-formulation for pulmonary drug release at SARS-CoV-2 interactive pH conditions.

Figure 5A:
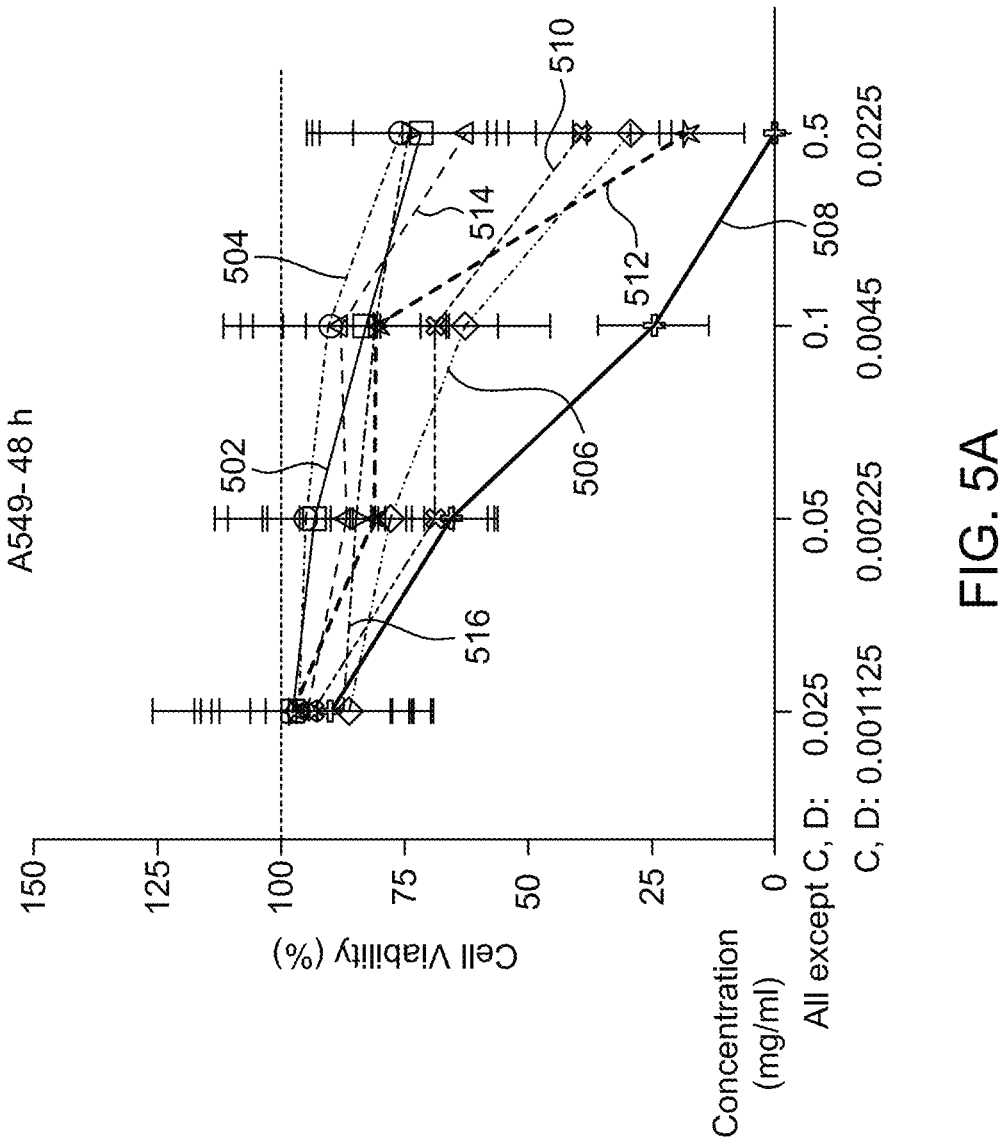
FIG. 5A shows cell viability assay of A549 cells treated with SPIONs/$MSSiO_2$/Chi (502), SPIONs/Hal/Chi (504), Cp (506), Rib (508), SPIONs/$MSSiO_2$/Chi/Cp (510), SPIONs/Hal/Chi/Cp (512), SPIONs/$MSSiO_2$/Chi/Cp/Rib (514), and SPIONs/Hal/Chi/Cp/Rib (516) for 48 hours, according to certain embodiments.
Figure 5B:
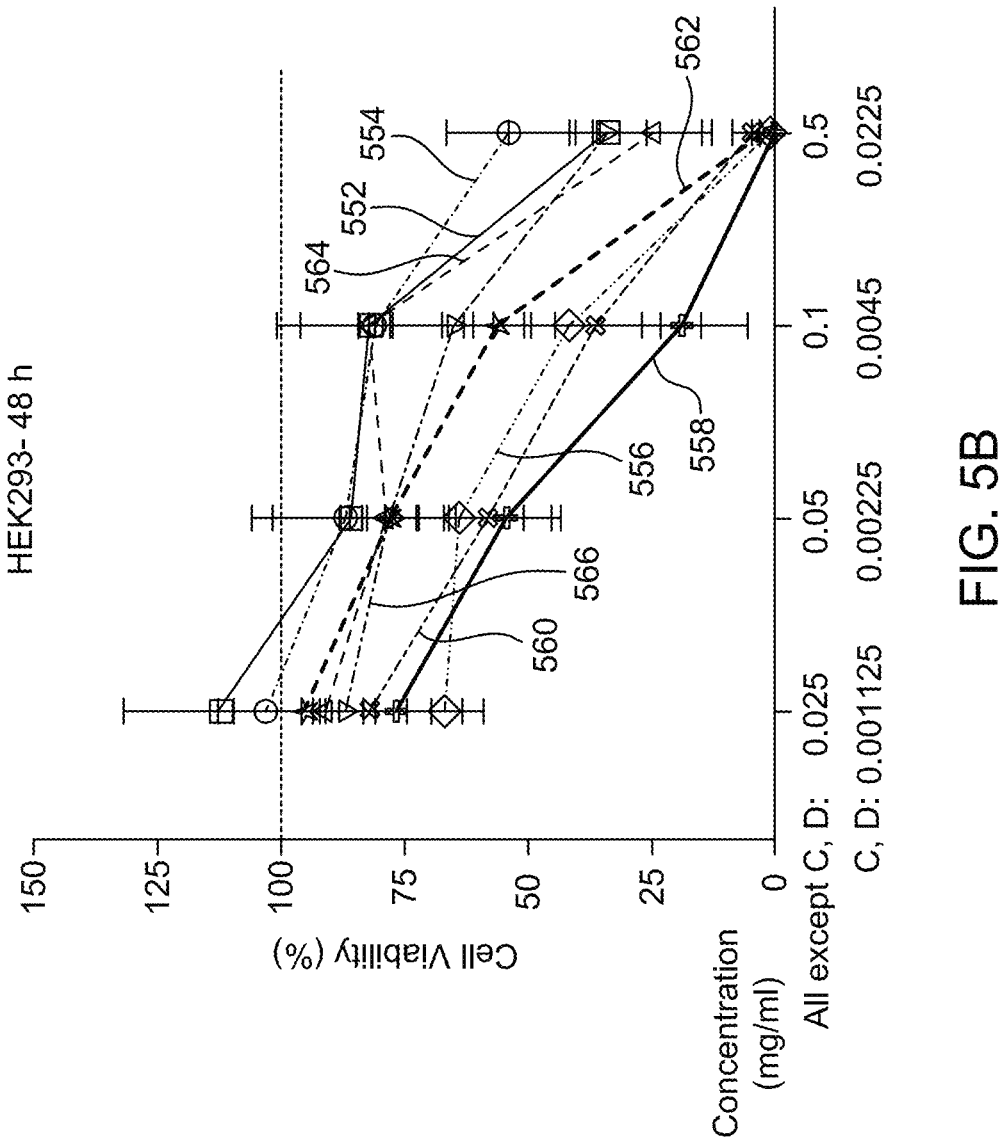
FIG. 5B shows cell viability assay of human embryonic kidney (HEK) 293 cells treated with SPIONs/$MSSiO_2$/Chi (552), SPIONs/Hal/Chi (554), Cp (556), Rib (558), SPIONs/ $MSSiO_2$/Chi/Cp (560), SPIONs/Hal/Chi/Cp (562), SPIONs/ $MSSiO_2$/Chi/Cp/Rib (564), and SPIONs/Hal/Chi/Cp/Rib (566) for 48 hours, according to certain embodiments.

The effect of the nanocomposites on cells was assessed in different cell lines: (i) A549 cells and (ii) HEK293 cells. FIG. 5A-FIG. 5B shows the cytotoxic potential of the nanocomposites using the MTT assay. In the case of A549 cells, nanocomposites containing SPIONs, chitosan, with either $MSSiO_2$ (502) or Hal (504), had little effects on viability compared to the no-treatment control. Cisplatin (506) and ribavirin (508) resulted in a significant reduction in cell viability. Cells treated with SPIONs, chitosan, and cisplatin with either $MSSiO_2$ (510) or Hal (512) had similar toxicity to the free cisplatin (506). Unexpectedly, adding ribavirin (514, 516) enhanced cell viability compared to free cisplatin or ribavirin.

On the other hand, HEK293 cells are more sensitive than the A549 cells, especially with nanocomposites containing the SPIONs, and chitosan, with either $MSSiO_2$ (552) or Hal (554) and the nanocomposites containing the SPIONs, chitosan, cisplatin, ribavirin, with either $MSSiO_2$ (564) or Hal (566). Unexpectedly, A549 cells treated with SPIONs/MSSiO₂/Chi/Cp/Rib (564) and SPIONs/Hal/Chi/Cp/Rib (566) still had better viability than those treated with free cisplatin and ribavirin. The results and statistical analysis are summarized in Table 2 below.

TABLE 2

Statistical analysis of the cell viability assay for A549 and HEK293 cells.

| Dose | Treatment Condition | A549 cells | | HEK293 cells | |
|---|---|---|---|---|---|
| | | Significant | P value | Significant | P value |
| 1 | SPIONs/MSSiO₂/Chi (A) | No | 0.9999 | No | 0.9772 |
| | SPIONs/Hal/Chi (B) | No | 0.9997 | No | 0.9989 |
| | Cp (C) | No | 0.921 | No | 0.1408 |
| | Rib (D) | No | 0.9722 | No | 0.5764 |
| | SPIONs/MSSiO₂/Chi/Cp (E) | No | 0.9976 | No | 0.62 |
| | SPIONs/Hal/Chi/Cp (F) | No | >0.9999 | No | 0.9978 |
| | SPIONs/MSSiO₂/Chi/Cp/Rib (G) | No | 0.9997 | No | 0.8549 |
| | SPIONs/Hal/Chi/Cp/Rib (H) | No | 0.7081 | No | 0.4946 |
| 2 | SPIONs/MSSiO₂/Chi (A) | No | 0.9986 | No | 0.9478 |
| | SPIONs/Hal/Chi (B) | No | 0.9987 | No | 0.8901 |
| | Cp (C) | No | 0.5239 | No | 0.4849 |
| | Rib (D) | No | 0.1735 | No | 0.162 |
| | SPIONs/MSSiO₂/Chi/Cp (E) | No | 0.3235 | No | 0.0724 |
| | SPIONs/Hal/Chi/Cp (F) | No | 0.9112 | No | 0.1589 |
| | SPIONs/MSSiO₂/Chi/Cp/Rib (G) | No | 0.9166 | No | 0.253 |
| | SPIONs/Hal/Chi/Cp/Rib (H) | No | 0.7063 | No | 0.4116 |
| 3 | SPIONs/MSSiO₂/Chi (A) | No | 0.8436 | No | 0.7216 |
| | SPIONs/Hal/Chi (B) | No | 0.9835 | No | 0.8606 |
| | Cp (C) | No | 0.4227 | No | 0.5954 |
| | Rib (D) | No | 0.0628 | Yes | 0.0076 |
| | SPIONs/MSSiO₂/Chi/Cp (E) | No | 0.3279 | No | 0.0526 |
| | SPIONs/Hal/Chi/Cp (F) | No | 0.9347 | No | 0.0676 |
| | SPIONs/MSSiO₂/Chi/Cp/Rib (G) | No | 0.9908 | Yes | 0.0128 |
| | SPIONs/Hal/Chi/Cp/Rib (H) | No | 0.6995 | No | 0.3088 |
| 4 | SPIONs/MSSiO₂/Chi (A) | No | 0.7567 | Yes | 0.0396 |
| | SPIONs/Hal/Chi (B) | No | 0.7009 | No | 0.1973 |
| | Cp (C) | Yes | 0.0422 | Yes | 0.0001 |
| | Rib (D) | Yes | <0.0001 | Yes | <0.0001 |
| | SPIONs/MSSiO₂/Chi/Cp (E) | No | 0.1614 | Yes | 0.0059 |
| | SPIONs/Hal/Chi/Cp (F) | No | 0.0555 | Yes | 0.0017 |
| | SPIONs/MSSiO₂/Chi/Cp/Rib (G) | No | 0.5827 | No | 0.0624 |
| | SPIONs/Hal/Chi/Cp/Rib (H) | No | 0.6693 | No | 0.2299 |

Figures 6A, 6B:
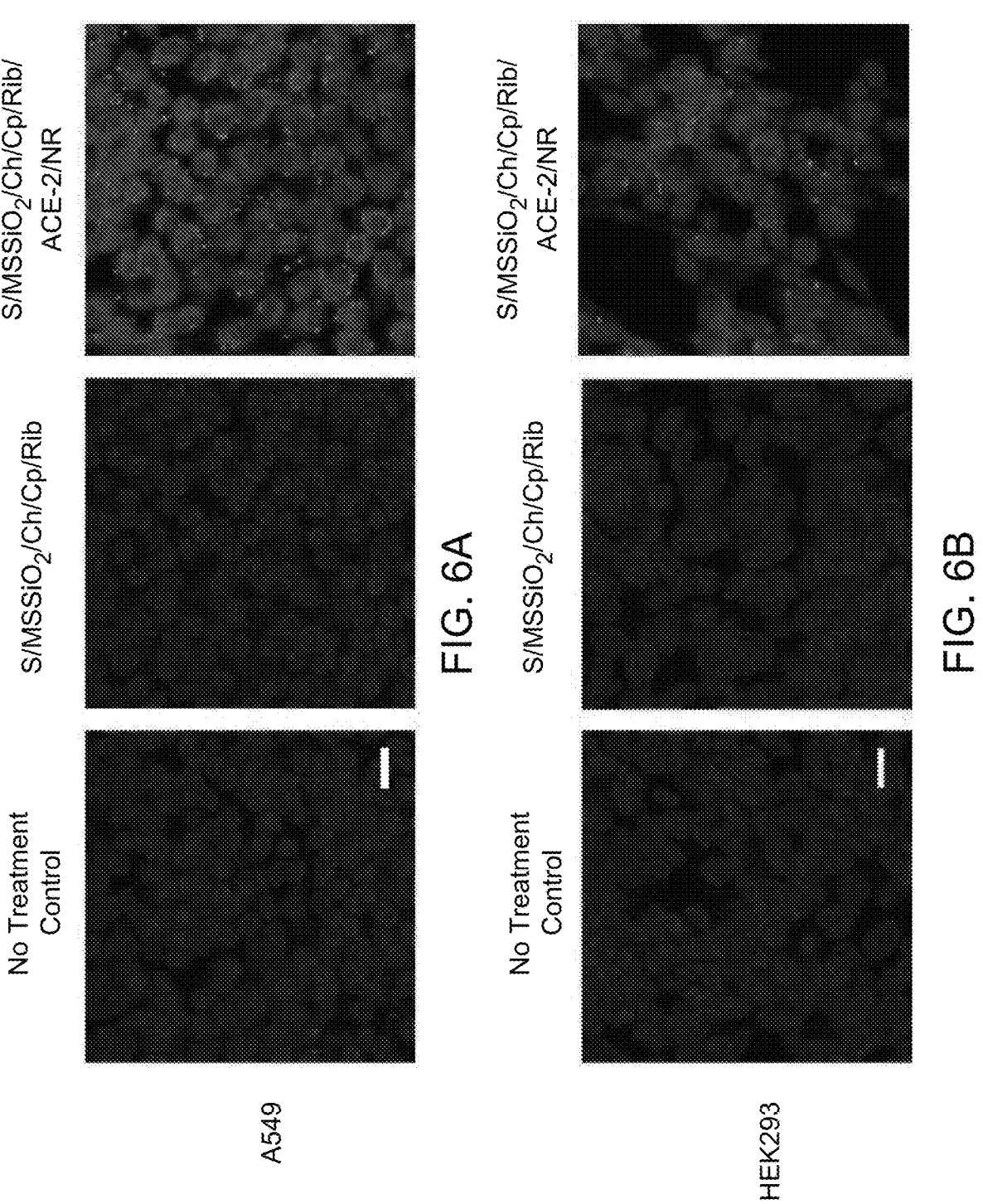
FIG. 6A shows an immunofluorescent image of A549 cells treated with SPIONs/$MSSiO_2$/Chi/Cp/Rib and SPIONs/$MSSiO_2$/Chi/Cp/Rib/ACE-2/Nile red (NR) at 0.1 milligrams per milliliters (mg/ml) for 24 hours in Hoechst and Nile red stains at scale bar 20 micrometers (μm), according to certain embodiments.
FIG. 6B shows an immunofluorescent image of HEK293 cells treated with SPIONs/$MSSiO_2$/Chi/Cp/Rib and SPIONs/$MSSiO_2$/Chi/Cp/Rib/ACE-2/NR at 0.1 mg/ml for 24 hours in Hoechst and Nile red stains at scale bar 20 μm, according to certain embodiments.

Furthermore, FIGS. 6A-6B show the investigation of whether the cells were able to internalize the nanocomposite successfully. SPIONs/MSSiO₂/Chi/Cp/Rib was functionalized with ACE-2 ligand and Nile Red (NR) dye. In addition, A549 and HEK293 cells were treated with the non-modified and modified nanocomposites (SPIONs/MSSiO₂/Chi/Cp/Rib and SPIONs/MSSiO₂/Chi/Cp/Rib/ACE-2/NR) and then stained with Hoechst. The examination was performed under a confocal fluorescent microscope. The assessment revealed the presence of pink speckles in cytoplasmic compartments of cells treated with the ACE-2/NR-functionalized nanocomposite but not in the cells treated with the non-functionalized version. These results indicated the successful internalization of the nanocomposites.

Numerous modifications and variations of the present disclosure are possible in light of the above teachings. It is therefore to be understood that within the scope of the appended claims, the invention may be practiced otherwise than as specifically described herein.

The invention claimed is:

1. A method of treating a COVID-19 infection, comprising:

administering to a subject in need thereof an effective amount of a composition, wherein the composition comprises:

silica nanoparticles;

superparamagnetic iron oxide nanoparticles (SPIONs), wherein the SPIONs consist of $Fe_3O_4$;

0.3-0.8 wt % chitosan;

cisplatin;

3-6 wt % ribavirin; and 0.1-0.6 wt % angiotensin-converting enzyme 2 (ACE-2), where wt % is based on the total weight of the composition, wherein the SPIONs and ACE-2 are dispersed on an outer surface of the silica nanoparticles, wherein the chitosan wraps around at least 20% of the surface area of the silica nanoparticles, wherein the cisplatin and ribavirin are in pores of the silica nanoparticles, wherein the composition is in the form of particles that are monodisperse, are spherical, and have an average diameter of 70-100 nm, wherein the composition has a BET surface area of 75-100 m²/g, wherein 72 hours after administering the composition, the composition releases 20-30% of the cisplatin at a pH of 5-6, wherein 72 hours after administering the composition, the composition releases 10-20% of the ribavirin at a pH of 5-6, wherein the chitosan only wraps around an external pore wall of the silica nanoparticles and does not block the pores of the silica nanoparticles, and wherein 30-60% of the surface area of the silica nanoparticles is covered with the chitosan, SPIONs, and ACE-2.

2. The method of claim 1, wherein the composition is administered into the tracheal mucus region of the subject in the form of a dry powder.

3. The method of claim 1, wherein the composition comprises 0.01-10 wt % of the cisplatin, based on a total weight of the composition.

4. The method of claim 1, wherein the composition comprises 5-20 wt % of the SPIONs, based on a total weight of the SPIONs and silica nanoparticles.

5. The method of claim 1, wherein the composition has an average pore size of 10-20 nm.

6. The method of claim 1, wherein the composition has an average pore volume of 0.25-0.35 $cm^3$/g.

7. The method of claim 1, wherein the composition has a saturation magnetization value of 8-9 emu/g.

8. The method of claim 1, wherein the chitosan is hydrogen bonded to the outer surface of the silica nanoparticles.

9. The method of claim 1, wherein 72 hours after administering the composition, the composition releases less than 15% of the cisplatin at a pH of 7-8.

10. The method of claim 1, wherein 72 hours after administering the composition, the composition releases less than 5% of the ribavirin at a pH of 7-8.

11. The method of claim 1, further comprising exposing the subject to an alternating magnetic field in a vicinity of a lung of the subject after administering the composition.

12. The method of claim 1, wherein the composition is administered into the tracheal mucus region of the subject in the form of a dry powder suspended in a fluid stream;

wherein during administering the composition, the composition is first fluidized in a container with a recirculating gas stream; then a controlled volume of the gas stream is released from the container into the oral or nasal passage of the subject, and wherein following administering the composition, the composition is internalized by at least one lung cell.

13. The method of claim 1, wherein the composition has a BET surface area of 75-85 $m^2$/g.

14. The method of claim 1, wherein the composition comprises 4-5 wt % ribavirin, based on a total weight of the composition.

15. The method of claim 1, wherein the composition comprises 0.5-0.6 wt % chitosan, based on the total weight of the composition.

16. The method of claim 1, wherein the composition comprises 0.2-0.4 wt % ACE-2, based on the total weight of the composition.

17. The method of claim 1, wherein the chitosan wraps around at least 40% of the surface area of the silica nanoparticles.

18. The method of claim 1, wherein 40-50% of the surface area of the silica nanoparticles is covered with the chitosan, SPIONs, and ACE-2.

19. The method of claim 1, wherein 72 hours after administering the composition, the composition releases 14-16% of the ribavirin at a pH of 5-6.

20. The method of claim 1, wherein administering the composition leads to a reduction in COVID-19 symptoms and wherein an effective amount of the composition is in a range of 0.1-30 g/kg.

* * * * *